United States Patent
Harvey

(10) Patent No.: US 11,497,621 B2
(45) Date of Patent: Nov. 15, 2022

(54) INSERTER FOR IMPLANTING A SPINAL IMPLANT

(71) Applicant: NuVasive, San Diego, CA (US)

(72) Inventor: Andrew Harvey, New York, CA (US)

(73) Assignee: NuVasive, Inc., San Diego, CA (US)

( * ) Notice: Subject to any disclaimer, the term of this patent is extended or adjusted under 35 U.S.C. 154(b) by 239 days.

(21) Appl. No.: 16/416,543

(22) Filed: May 20, 2019

(65) Prior Publication Data

US 2019/0271997 A1 Sep. 5, 2019

Related U.S. Application Data

(63) Continuation of application No. 15/677,981, filed on Aug. 15, 2017, now Pat. No. 10,335,287, which is a continuation of application No. 14/597,085, filed on Jan. 14, 2015, now Pat. No. 9,730,802.

(60) Provisional application No. 62/009,647, filed on Jun. 9, 2014, provisional application No. 61/927,421, filed on Jan. 14, 2014.

(51) Int. Cl.
*A61F 2/46* (2006.01)

(52) U.S. Cl.
CPC .............. *A61F 2/4611* (2013.01); *A61F 2/46* (2013.01)

(58) Field of Classification Search
CPC ................ A61F 2/4611; A61F 2/46; A61B 2017/00477; A61B 2017/0046; A61B 2017/00473; F16L 37/248; F16L 37/24
See application file for complete search history.

(56) References Cited

U.S. PATENT DOCUMENTS

| 5,015,247 A | | 5/1991 | Michelson | |
|---|---|---|---|---|
| 5,443,514 A | * | 8/1995 | Steffee | A61F 2/447 128/898 |
| D377,095 S | | 12/1996 | Michelson | |
| D377,096 S | | 12/1996 | Michelson | |
| D377,527 S | | 1/1997 | Michelson | |
| 5,593,409 A | | 1/1997 | Michelson | |
| 5,609,635 A | | 3/1997 | Michelson | |
| 5,653,762 A | * | 8/1997 | Pisharodi | A61B 17/025 606/86 A |
| 5,658,337 A | | 8/1997 | Kohrs | |
| D392,387 S | | 3/1998 | Michelson | |
| 5,772,661 A | | 6/1998 | Michelson | |
| 5,776,199 A | | 7/1998 | Michelson | |
| 5,785,710 A | | 7/1998 | Michelson | |
| 5,860,973 A | | 1/1999 | Michelson | |
| 5,885,299 A | * | 3/1999 | Winslow | A61F 2/4637 606/99 |
| 5,888,224 A | * | 3/1999 | Beckers | A61F 2/4611 623/17.16 |

(Continued)

FOREIGN PATENT DOCUMENTS

AU 199944738 A1 11/1999
AU 200036361 B2 7/2000

(Continued)

*Primary Examiner* — David W Bates
(74) *Attorney, Agent, or Firm* — Hoffman Warnick LLC

(57) ABSTRACT

The present invention relates generally to medical devices, systems, and methods for use in surgery. In particular, the disclosed system and methods relate to an intervertebral spinal implant sized and dimensioned for the lumbar spine implantable via a posterior approach. The system includes an implant, instruments for delivering the implant.

18 Claims, 11 Drawing Sheets

(56) References Cited

U.S. PATENT DOCUMENTS

| | | |
|---|---|---|
| 5,961,554 A | 10/1999 | Janson |
| D425,989 S | 5/2000 | Michelson |
| 6,066,174 A | 5/2000 | Farris |
| 6,113,602 A * | 9/2000 | Sand ................. A61B 17/1757 |
| | | 606/279 |
| 6,120,502 A | 9/2000 | Michelson |
| 6,123,705 A | 9/2000 | Michelson |
| 6,136,001 A | 10/2000 | Michelson |
| 6,139,551 A | 10/2000 | Michelson |
| D437,055 S | 1/2001 | Michelson |
| 6,190,388 B1 | 2/2001 | Michelson |
| 6,210,412 B1 | 4/2001 | Michelson |
| 6,241,770 B1 | 6/2001 | Michelson |
| 6,290,724 B1 | 9/2001 | Marino |
| 6,350,283 B1 | 2/2002 | Michelson |
| 6,364,880 B1 | 4/2002 | Michelson |
| 6,395,031 B1 | 5/2002 | Foley |
| D460,189 S | 7/2002 | Michelson |
| 6,423,095 B1 | 7/2002 | Van Hoeck |
| D463,560 S | 9/2002 | Michelson |
| 6,447,544 B1 | 9/2002 | Michelson |
| 6,478,823 B1 | 11/2002 | Michelson |
| 6,485,517 B1 | 11/2002 | Michelson |
| 6,500,205 B1 | 12/2002 | Michelson |
| 6,520,967 B1 | 2/2003 | Cauthen |
| 6,527,773 B1 | 3/2003 | Lin |
| 6,537,320 B1 | 3/2003 | Michelson |
| 6,558,423 B1 | 5/2003 | Michelson |
| 6,572,654 B1 | 6/2003 | Santilli |
| 6,575,899 B1 | 6/2003 | Foley |
| 6,595,995 B2 * | 7/2003 | Zdeblick ............... A61L 27/227 |
| | | 606/80 |
| 6,599,291 B1 | 7/2003 | Foley |
| 6,605,089 B1 | 8/2003 | Michelson |
| 6,610,065 B1 | 8/2003 | Branch |
| 6,746,454 B2 * | 6/2004 | Winterbottom ....... A61F 2/4455 |
| | | 606/99 |
| 6,758,849 B1 | 7/2004 | Michelson |
| 6,830,570 B1 | 12/2004 | Frey |
| 6,942,697 B2 | 9/2005 | Lange |
| 7,008,453 B1 | 3/2006 | Michelson |
| 7,070,598 B2 | 7/2006 | Lim |
| 7,087,055 B2 | 8/2006 | Lim |
| 7,094,239 B1 | 8/2006 | Michelson |
| 7,115,143 B1 | 10/2006 | Michelson |
| 7,244,275 B2 | 7/2007 | Michelson |
| 7,291,149 B1 | 11/2007 | Michelson |
| 7,326,248 B2 | 2/2008 | Michelson |
| 7,354,452 B2 | 4/2008 | Foley |
| 7,452,359 B1 | 11/2008 | Michelson |
| 7,462,195 B1 | 12/2008 | Michelson |
| 7,470,273 B2 | 12/2008 | Dougherty-Shah |
| 7,491,205 B1 | 2/2009 | Michelson |
| 7,503,935 B2 | 3/2009 | Zucherman |
| 7,534,254 B1 | 5/2009 | Michelson |
| 7,578,820 B2 | 8/2009 | Moore |
| 7,594,919 B2 | 9/2009 | Peterman |
| 7,608,105 B2 | 10/2009 | Pavlov |
| 7,608,107 B2 | 10/2009 | Michelson |
| 7,618,423 B1 | 11/2009 | Valentine |
| 7,776,049 B1 | 8/2010 | Curran |
| 7,815,682 B1 | 10/2010 | Peterson |
| 7,867,277 B1 | 1/2011 | Tohmeh |
| 7,901,458 B2 | 3/2011 | Deridder |
| 7,905,886 B1 | 3/2011 | Curran |
| 7,976,549 B2 | 7/2011 | Dye |
| 7,988,699 B2 | 8/2011 | Martz |
| 8,002,837 B2 * | 8/2011 | Stream ................. A61F 2/4684 |
| | | 623/17.16 |
| 8,012,208 B2 | 9/2011 | Lechmann |
| 8,070,754 B2 | 12/2011 | Fabian |
| 8,075,622 B2 | 12/2011 | Van Hoeck |
| 8,097,027 B2 | 1/2012 | Lim |
| 8,105,383 B2 | 1/2012 | Michelson |
| 8,109,935 B2 | 2/2012 | Stoffel |
| 8,114,088 B2 * | 2/2012 | Miller ................. A61F 2/4611 |
| | | 606/90 |
| 8,114,092 B2 | 2/2012 | Altarac |
| 8,114,162 B1 | 2/2012 | Bradley |
| 8,123,757 B2 | 2/2012 | Zalenski |
| 8,137,403 B2 | 3/2012 | Michelson |
| 8,221,503 B2 | 7/2012 | Garcia |
| 8,252,060 B2 | 8/2012 | Hansell |
| 8,262,736 B2 | 9/2012 | Michelson |
| 8,298,235 B2 | 10/2012 | Grinberg |
| 8,303,601 B2 * | 11/2012 | Bandeira ............. A61B 17/025 |
| | | 606/99 |
| 8,308,805 B2 * | 11/2012 | Lynn ..................... A61F 2/447 |
| | | 623/17.16 |
| 8,317,798 B2 | 11/2012 | Lim |
| 8,349,017 B2 | 1/2013 | Marnay |
| 8,377,071 B2 | 2/2013 | Lim |
| 8,377,137 B2 | 2/2013 | Sournac |
| 8,382,840 B2 | 2/2013 | Hestad |
| 8,409,292 B2 | 4/2013 | Michelson |
| 8,425,529 B2 | 4/2013 | Milz |
| 8,454,623 B2 * | 6/2013 | Patel .................... A61F 2/4611 |
| | | 606/99 |
| 8,500,749 B2 | 8/2013 | Lee |
| 8,500,813 B2 | 8/2013 | Foley |
| 8,540,725 B2 | 9/2013 | Lim |
| 8,579,904 B2 * | 11/2013 | Siccardi ............... A61F 2/4611 |
| | | 606/86 A |
| 8,579,907 B2 | 11/2013 | Lim |
| 8,603,175 B2 | 12/2013 | Thibodeau |
| 8,617,244 B2 | 12/2013 | Reichen |
| 8,623,088 B1 | 1/2014 | Tohmeh |
| 8,668,741 B2 | 3/2014 | Michelson |
| 8,679,118 B2 | 3/2014 | Michelson |
| 8,696,752 B2 | 4/2014 | Shih |
| 8,734,447 B1 | 5/2014 | Michaelson |
| 8,771,321 B2 | 7/2014 | Michelson |
| 8,790,403 B2 | 7/2014 | Flickinger |
| 8,801,721 B2 | 8/2014 | Berry |
| 8,828,018 B2 * | 9/2014 | Ragab .................... A61F 2/447 |
| | | 606/99 |
| 8,845,738 B2 | 9/2014 | Michelson |
| 8,882,843 B2 | 11/2014 | Michelson |
| 8,882,844 B2 | 11/2014 | Mcclintock |
| 8,926,701 B2 | 1/2015 | De Luria |
| 8,986,389 B2 | 3/2015 | Lim |
| 8,998,920 B2 | 4/2015 | Berry |
| 9,028,553 B2 | 5/2015 | Lindenmann |
| 9,034,043 B2 * | 5/2015 | Danacioglu ............ A61F 2/447 |
| | | 623/17.16 |
| D731,063 S | 6/2015 | VerHage |
| D733,303 S | 6/2015 | Peterson |
| D741,488 S | 10/2015 | Tohmeh |
| 9,241,810 B1 | 1/2016 | Rumi |
| 9,248,028 B2 | 2/2016 | Gamache |
| 9,248,029 B2 | 2/2016 | Bergey |
| 9,339,395 B2 * | 5/2016 | Prado .................... A61F 2/4455 |
| 2003/0060886 A1 | 3/2003 | Van Hoeck |
| 2003/0130667 A1 | 7/2003 | Lin |
| 2003/0195632 A1 | 10/2003 | Foley |
| 2004/0078079 A1 * | 4/2004 | Foley ................. A61B 17/025 |
| | | 623/17.11 |
| 2004/0102847 A1 | 5/2004 | Sato |
| 2004/0162616 A1 * | 8/2004 | Simonton ............. A61F 2/4684 |
| | | 623/17.11 |
| 2004/0186572 A1 | 9/2004 | Lange et al. |
| 2005/0027360 A1 | 2/2005 | Webb |
| 2005/0070900 A1 | 3/2005 | Serhan |
| 2005/0096745 A1 | 5/2005 | Andre |
| 2005/0267578 A1 | 12/2005 | Michelson |
| 2006/0129238 A1 * | 6/2006 | Paltzer .................. A61F 2/447 |
| | | 623/17.11 |
| 2006/0167548 A1 | 7/2006 | Jackson |
| 2006/0195190 A1 | 8/2006 | Lechmann et al. |
| 2007/0032872 A1 | 2/2007 | Simonton |
| 2007/0162138 A1 | 7/2007 | Heinz |
| 2007/0173857 A1 | 7/2007 | Trieu |
| 2007/0260315 A1 | 11/2007 | Foley |

(56) References Cited

U.S. PATENT DOCUMENTS

| | | | |
|---|---|---|---|
| 2008/0221695 A1* | 9/2008 | Jacofsky | A61F 2/447 623/17.16 |
| 2008/0269756 A1* | 10/2008 | Tomko | A61B 17/1757 606/87 |
| 2009/0062917 A1 | 3/2009 | Foley et al. | |
| 2009/0112220 A1* | 4/2009 | Kraus | A61F 2/4455 606/99 |
| 2009/0187246 A1 | 7/2009 | Foley | |
| 2009/0187247 A1 | 7/2009 | Metcalf | |
| 2009/0270989 A1 | 10/2009 | Conner | |
| 2009/0276048 A1 | 11/2009 | Chirico | |
| 2010/0114105 A1* | 5/2010 | Butters | A61F 2/447 606/99 |
| 2010/0152857 A1 | 6/2010 | Freeman | |
| 2010/0204798 A1 | 8/2010 | Gerbec | |
| 2011/0071637 A1 | 3/2011 | Muhanna | |
| 2011/0106261 A1* | 5/2011 | Chin | A61F 2/4455 623/17.16 |
| 2011/0166654 A1 | 7/2011 | Gately | |
| 2011/0190892 A1* | 8/2011 | Kirschman | A61F 2/447 623/17.16 |
| 2011/0230969 A1 | 9/2011 | Biedermann | |
| 2011/0276139 A1 | 11/2011 | Mahoney | |
| 2012/0071977 A1* | 3/2012 | Oglaza | A61B 17/8858 623/17.11 |
| 2012/0078370 A1 | 3/2012 | James | |
| 2012/0083885 A1* | 4/2012 | Thibodeau | A61F 2/4611 623/17.16 |
| 2012/0143341 A1 | 6/2012 | Zipnick | |
| 2012/0165943 A1 | 6/2012 | Mangione | |
| 2012/0165945 A1 | 6/2012 | Hansell | |
| 2012/0290094 A1 | 11/2012 | Lim | |
| 2013/0006365 A1 | 1/2013 | Pepper | |
| 2013/0226244 A1 | 8/2013 | Davenport | |
| 2013/0282126 A1 | 10/2013 | Saidha | |
| 2013/0320672 A1* | 12/2013 | Steele | F16L 37/248 285/305 |
| 2014/0012383 A1 | 1/2014 | Triplett | |
| 2014/0031943 A1 | 1/2014 | Yu | |
| 2014/0058400 A1 | 2/2014 | Dudasik | |
| 2014/0058518 A1 | 2/2014 | Niemiec | |
| 2014/0100662 A1 | 4/2014 | Patterson | |
| 2014/0148907 A1 | 5/2014 | Gately | |
| 2014/0316477 A1 | 10/2014 | Milz | |
| 2014/0330280 A1* | 11/2014 | Markworth | A61B 17/025 606/90 |
| 2014/0350682 A1 | 11/2014 | Bagga | |
| 2015/0012098 A1 | 1/2015 | Eastlack | |
| 2015/0012099 A1 | 1/2015 | Baccelli | |
| 2015/0051702 A1 | 2/2015 | Chataigner | |
| 2015/0051705 A1 | 2/2015 | James | |
| 2015/0066145 A1 | 3/2015 | Rogers | |
| 2015/0073421 A1 | 3/2015 | Siegal | |
| 2015/0081021 A1 | 3/2015 | Ciupik | |
| 2015/0100129 A1 | 4/2015 | Waugh | |
| 2015/0105860 A1 | 4/2015 | Garner | |
| 2015/0112442 A1 | 4/2015 | Foley | |
| 2015/0127108 A1 | 5/2015 | Michelson | |
| 2015/0157469 A1* | 6/2015 | Prado | A61F 2/4601 606/86 A |
| 2015/0257894 A1 | 9/2015 | Levy | |
| 2017/0172758 A1 | 6/2017 | Field | |

FOREIGN PATENT DOCUMENTS

| | | |
|---|---|---|
| AU | 200036471 B2 | 7/2000 |
| AU | 200133420 A1 | 6/2001 |
| AU | 200165603 A1 | 10/2001 |
| AU | 200215574 A1 | 3/2002 |
| AU | 2008202022 A1 | 5/2008 |
| CA | 1337842 | 1/1996 |
| CA | 2168835 | 8/1996 |
| CA | 2447257 | 12/1996 |
| DE | 102010023437 | 1/2011 |
| WO | WO-1990000037 | 1/1990 |
| WO | WO-1995026164 | 10/1995 |
| WO | WO-1996039988 | 12/1996 |
| WO | WO-2000023015 | 4/2000 |
| WO | WO-2001080784 | 11/2001 |
| WO | WO-2002078514 | 10/2002 |

* cited by examiner

INSERTER FOR IMPLANTING A SPINAL IMPLANT

CROSS REFERENCES TO RELATED APPLICATIONS

The present application is a continuation of U.S. patent application Ser. No. 15/677,981 filed on Aug. 15, 2017 now U.S. Pat. No. 10,335,287, which is a continuation of U.S. patent application Ser. No. 14/597,085, filed on Jan. 14, 2015 (now U.S. Pat. No. 9,730,802), which claims the benefit of priority from U.S. Provisional Patent Application No. 61/927,421, filed on Jan. 14, 2014, and U.S. Provisional Patent Application No. 62/009,647 filed on Jun. 9, 2014, the entire contents of which are hereby expressly incorporated by reference into this disclosure as if set forth in their entirety herein.

FIELD

The present invention relates generally to spinal surgery and, more particularly, to a device for spinal fusion comprising a spinal fusion implant of non-bone construction to be introduced into any variety of spinal target sites.

BACKGROUND

Currently there nearly 500,000 spine fusion procedures performed each year in the United States. One of the causes of back pain and disability derives from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Minimally invasive methods of performing spinal fusion have gained popularity in recent years due to the many benefits of the procedure which include diminished dissection of body tissue and lower blood loss during surgery resulting in reduced surgery time, lower post-operative pain and a quicker recovery for patients. Transforaminal lumbar interbody fusion (TLIF) procedures provide unilateral access to a desired target site. The TLIF technique involves approaching the spine in a similar manner as a posterior approach but more from the left or right of the spine through a midline incision in a patient's back. This procedure requires only one incision in the back of a patient and involves placing a fusion device into the intervertebral disc space. Introducing the intervertebral implant serves to restore the height ("disc height") between adjacent vertebrae, which reduces if not eliminates neural impingement commonly associated with a damaged or diseased disc.

SUMMARY OF THE INVENTION

The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant of the present invention may be provided in any number of suitable shapes and sizes depending upon the particular surgical procedure or need. The spinal fusion implant may be dimensioned for use in any part of the spine (e.g. cervical, lumbar and/or thoracic) without departing from the scope of the present invention. The implant may be dimensioned, by way of example only, having a width ranging between 8 and 14 mm, a height ranging between 8 and 18 mm, and a length ranging between 25 and 45 mm.

According to one broad aspect of the present invention, the spinal fusion implant includes a top surface, a bottom surface, lateral sides, a proximal end, and a distal end. The spinal fusion implant of the present invention may be used to provide temporary or permanent fixation along an orthopedic target site. To do so, the spinal fusion implant may be introduced into a disc space while locked to a surgical insertion instrument and thereafter manipulated in the proper orientation and released. Once deposited in the disc space, the spinal fusion implant of the present invention effects fusion over time as the natural healing process integrates and binds the implant.

The spinal fusion implant of the present invention may be provided with any number of additional features for promoting fusion, such as one or more apertures extending between the top and bottom surfaces which allow a boney bridge to form through the spinal fusion implant. The spinal implant may also be preferably equipped with one or more lateral openings which facilitate visualization at the time of implantation and at subsequent clinical evaluations.

The spinal fusion implant may also be provided with any number of suitable anti-migration features to prevent the implant from migrating or moving from the disc space after implantation. Suitable anti-migration features may include, but are not necessarily limited to, angled teeth or ridges formed along the top and bottom surfaces of the implant and/or rod elements disposed within the distal and/or proximal ends.

The spinal fusion implant may be provided with one or more radiographic markers at the proximal and/or distal ends. These markers allow for a more detailed visualization of the implant during and after insertion (through radiography) and allow for a more accurate and effective placement of the implant.

The proximal end of the spinal fusion implant may be provided with a surface that is tapered (angled) to avoid dural impingement after implantation. Additionally, the tapered nature of the proximal surface can aid in overall fit of the spinal fusion implant within the intervertebral disc space. Significantly, the tapered proximal surface on the proximal end enables the spinal fusion implant to maximize contact with the posterior portion of the cortical ring of each adjacent vertebral body.

The distal end of the spinal fusion implant may be provided with a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during certain methods of insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies. The distal end of the spinal fusion implant may be at least partially asymmetrically curved about the longitudinal axis to approximate the anterior portion of the cortical ring of each adjacent vertebral body when the implant is placed in its desired final oblique position.

The spinal fusion implant may be provided with a variable height along at least a portion of the implant. In one embodiment, the variable height tapers in a direction oblique to both the length and width of the implant. The oblique taper imparts a greater height to the anterior aspect of the intervertebral disc space when the spinal fusion implant is positioned obliquely within the disc space. Imparting a greater height to the anterior aspect of the disc space restores the natural lordotic curvature of the lumbar spine.

The spinal fusion implant may be provided with at least one set of variable opposing corner rounds varying in their radii along the length of the implant to allow for more gradual lead-in at the distal end which facilitates easier and safer insertion of the spinal fusion implant.

The spinal fusion implant may be further provided with asymmetric convex top and bottom surfaces between first and second lateral sides to approximate the anatomical concavities of the inferior endplate of the superior vertebra and the superior endplate of the inferior vertebra.

The spinal fusion implant may be further provided with asymmetrically convex top and bottom surfaces along the length of the implant between proximal and distal ends of the implant. The asymmetric curvature enables the spinal fusion implant to even better match the anatomical concavities of the inferior endplate of the superior vertebra and the superior endplate of the inferior vertebra.

The spinal fusion implant may be introduced into a spinal target site through use of any of a variety of suitable surgical instruments having the capability to engage the implant. The spinal fusion implant is capable of being used in minimally invasive surgical procedures, needing only a relatively small operative corridor for insertion.

The spinal fusion implant may be inserted into the intervertebral space and rotated into final position. Once the implant has been positioned in its desired location within the intervertebral space, the user will then rotate the implant 90° such that the top and bottom surfaces face in a caudad/cephalad direction and the anti-migration features engage the vertebral bodies. Significantly, the direction of rotation is critical to ensure proper placement of the implant such that the edges of the proximal surface rest on the cortical ring of the vertebral bodies and the proximal surface does not protrude into the spinal canal. For example, if the spinal fusion implant approaches a patient's spine posteriorly from the right with the (longer) first lateral side facing caudally, then implant must be rotated in a counter-clockwise direction to achieve proper positioning.

A single spinal fusion implant may be provided and inserted into an intervertebral disc space and positioned obliquely across the disc space such that the proximal and distal ends are on opposite sides of the midline of the intervertebral space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 21 B is an example lateral x-ray indicating the position of radiographic markers of the spinal fusion implant placed in the configuration shown in FIG. 21 A;

FIG. 22 B is an example of a lateral x-ray indicating the position of radiographic markers of the spinal fusion implant in the desired oblique configuration as shown FIG. 22 A.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant, system, and methods disclosed herein boasts a variety of inventive features and components that warrant patent protection, both individually and in combination.

Figure 1:
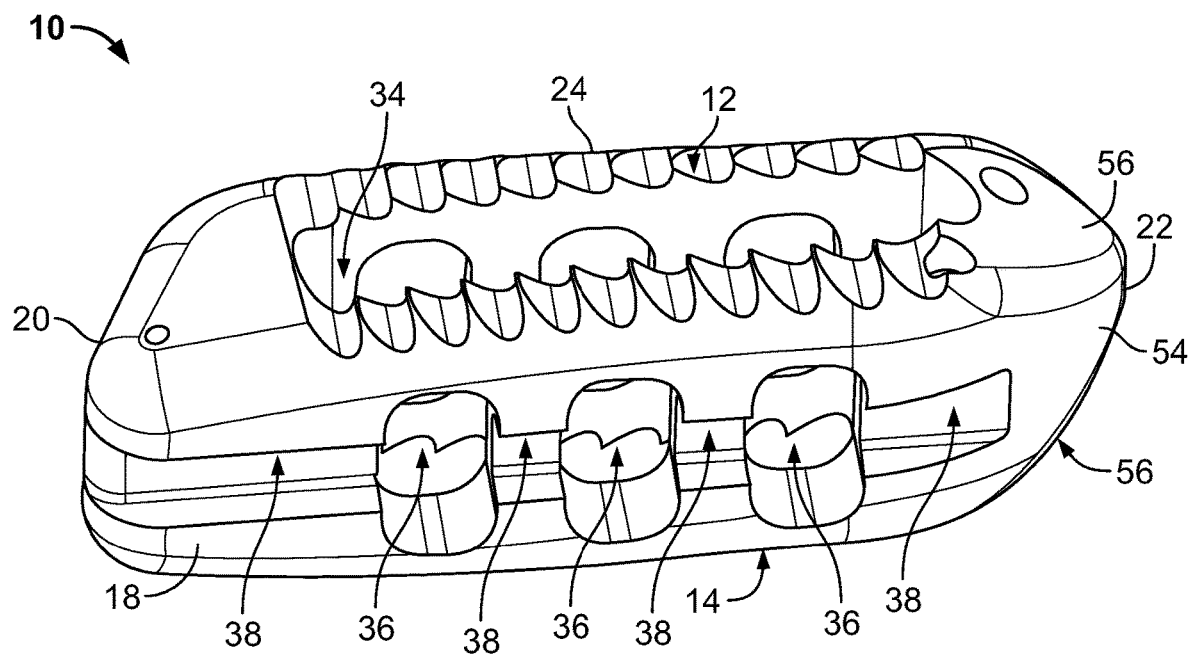
FIG. 1 is a perspective view of an example of a spinal fusion implant according to one embodiment of the present invention.
Figure 2:
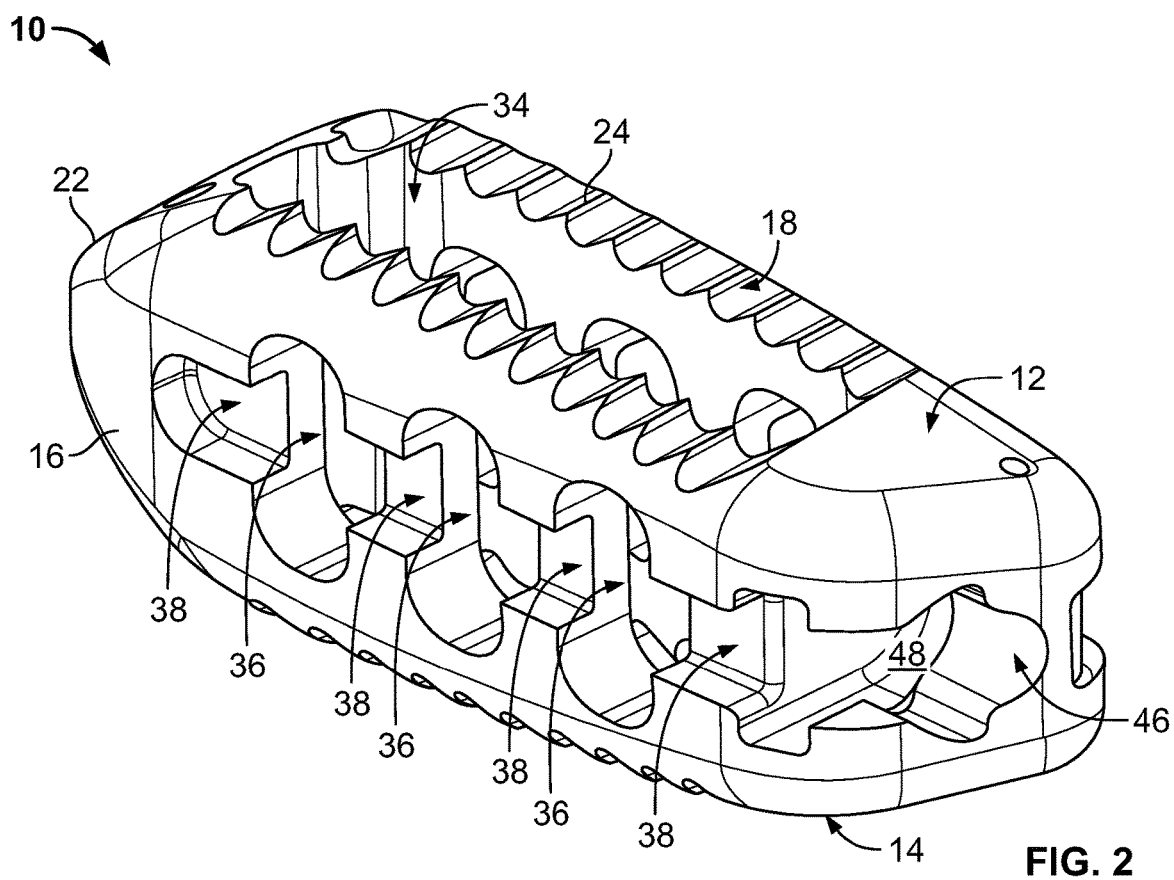
FIG. 2 is a second perspective view of the spinal fusion implant of FIG. 1.

FIGS. 1-2 illustrate a spinal fusion implant 10 according to a first broad aspect of the present invention. The spinal fusion implant 10 may be constructed of any suitable non-bone composition, including but not limited to polymer compositions (e. g. poly-ether-ether-ketone (PEEK) and/or poly-ether-ketone-ketone (PEKK)), ceramic, metal and/or any combination of polymer compositions, ceramic and metal. The spinal fusion implant may be provided with a surface coating (for example, titanium plasma spray) to encourage bone growth onto endplate contacting surfaces. The spinal fusion implant 10 of the present invention may be provided in any number of shapes and sizes depending upon the particular surgical procedure or need. By way of example only, the spinal fusion implant 10 may have a width ranging between 8 and 14 mm, a height ranging between 6 and 18 mm, and a length ranging between 20 and 45 mm.

The spinal fusion implant 10 of the present invention includes a top surface 12, a bottom surface 14, first and second lateral sides 16, 18, a proximal (posterior) end 20 and a distal (anterior) end 22. The spinal fusion implant 10 of the present invention may be used to provide temporary or permanent fixation within an orthopedic target site. To do so, the spinal fusion implant 10 may be introduced into a disc space while locked to a surgical insertion instrument and thereafter employed in the proper orientation and released, as explained in further detail below. Once deposited in the disc space, the spinal fusion implant 10 of the present invention effects spinal fusion over time as the natural healing process integrates and binds the implant.

Figure 3:
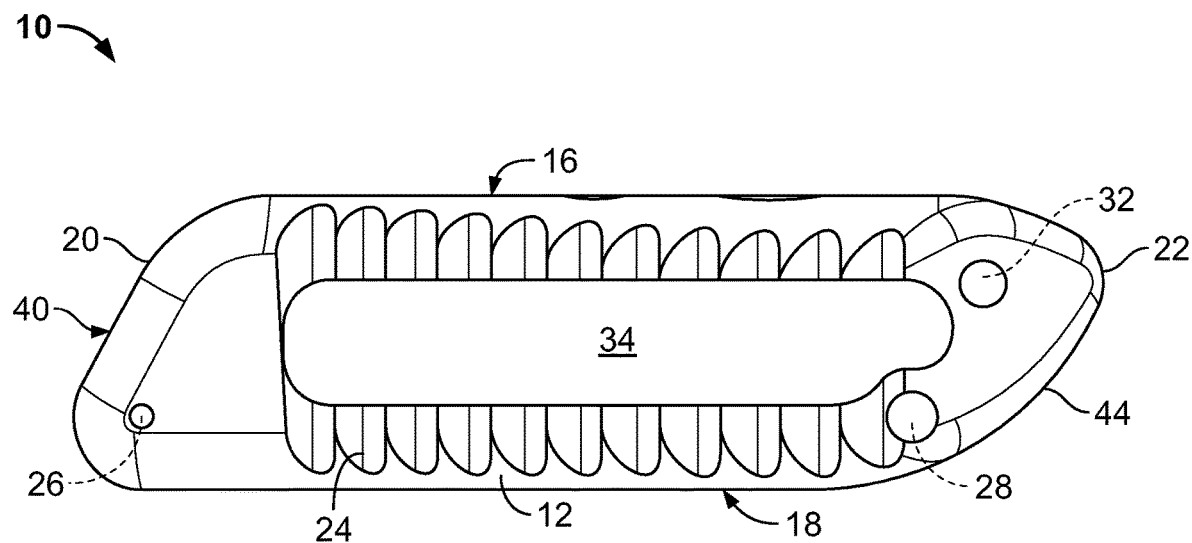
FIG. 3 is a top view of the spinal fusion implant of FIG. 1.
Figure 4:
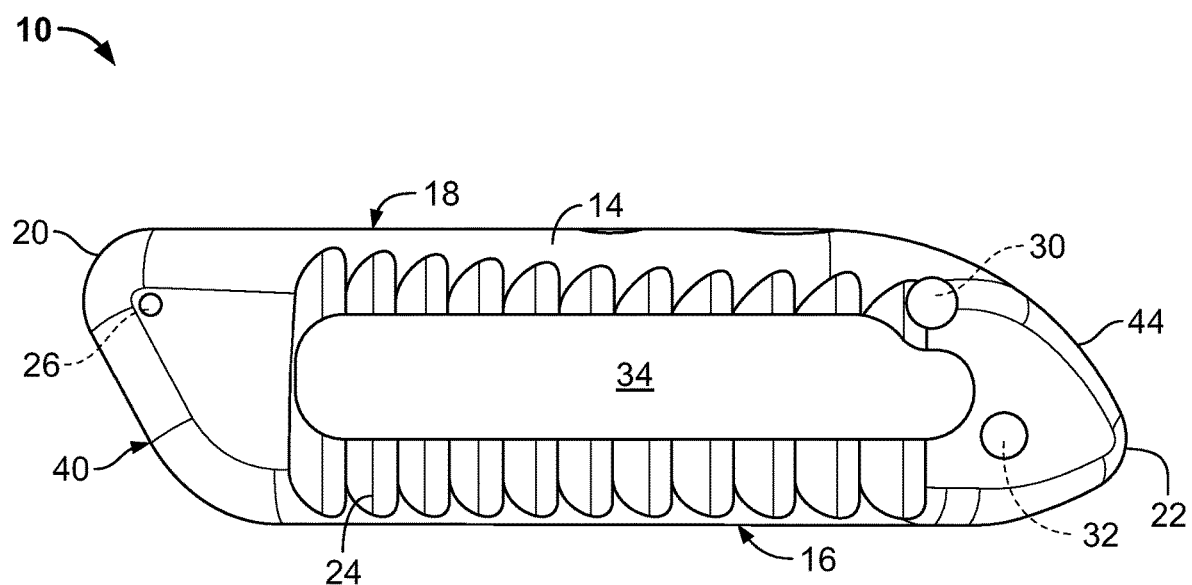
FIG. 4 is a bottom view of the spinal fusion implant of FIG. 1.

FIGS. 3-4 illustrate the top and bottom surfaces 12, 14, respectively, of the spinal fusion implant 10. The top and bottom surfaces 12, 14 are configured to engage the vertebral bodies adjoining the target disc space. Accordingly, the top and bottom surfaces 12, 14 each preferably include a plurality of anti-migration features designed to increase the friction between the spinal fusion implant 10 and the adjacent contacting surfaces of the vertebral bodies. Such anti-migration features may include ridges (or teeth) 24 provided along the top surface 12 and/or bottom surface 14. The friction prohibits migration of the implant 10 after insertion into the intervertebral space and during the propagation of natural bony fusion. It should be appreciated by one skilled in the art that such ridges (or teeth) 24 can be oriented in a particular direction which will stabilize the implant in several degrees of rotation during placement.

The spinal fusion implant 10 of the present invention may also be provided with one or more radiographic markers to allow for visual determination of proper implant placement. The radiographic markers may be manufactured from any of a variety of suitable radiopaque materials, including but not limited to a metal, ceramic, and/or polymer material, preferably having radiopaque characteristics. The radiographic markers may be provided in any size or shape suitable to facilitate effective and accurate visualization of implant placement.

The spinal fusion implant 10 include radiographic markers in the form of elongated cylinders extending generally perpendicularly through the implant 10 between the top and bottom surfaces 12, 14. Alternatively, radiographic markers may include a shorter element which extends only partially from either the top surface 12 or the bottom surface 14 (that is, does not extend through the entire height of the implant 10). As a further alternative, radiographic markers may extend at least partially (but not fully) toward either or both of top and bottom surfaces 12, 14 (that is, radiographic markers may be disposed completely within the body of the implant 10).

Figure 7:
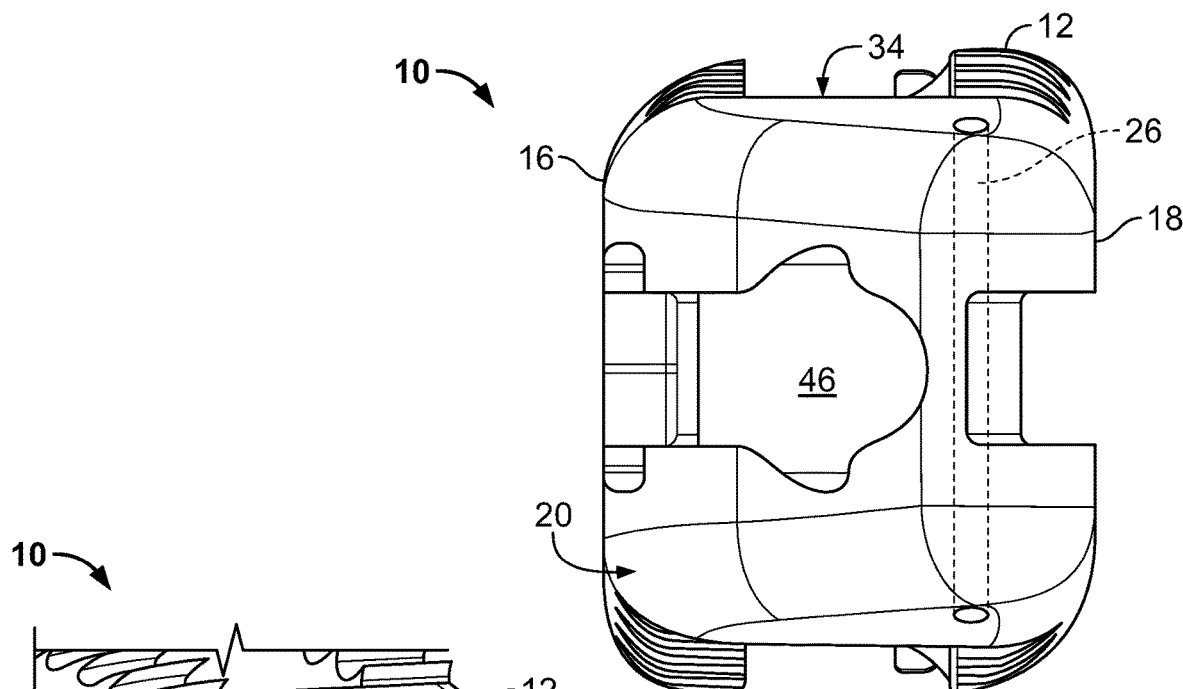
FIG. 7 is a plan view of a proximal end of the spinal fusion implant of FIG. 1.
Figure 10:
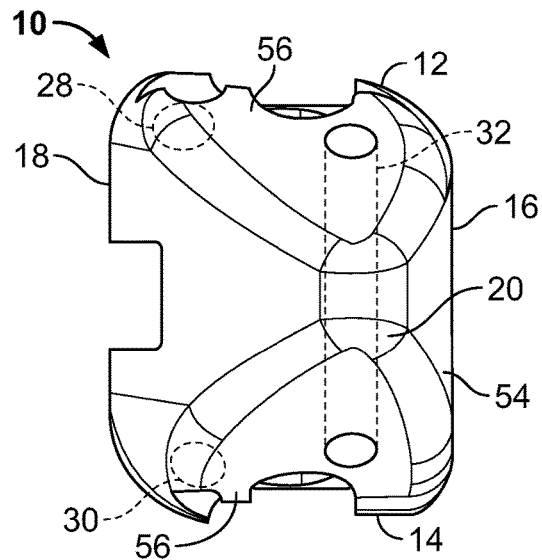
FIG. 10 is a plan view of a distal end of the spinal fusion implant of FIG. 1.

As best appreciated in FIGS. 7 and 10, the proximal end 20 of the spinal fusion implant 10 may be provided with at least one radiographic marker 26 positioned extending at least partially through the implant between top and bottom surfaces 12, 14 near the intersection of second lateral side 18 and proximal surface 40. Radiographic marker 26 may preferably indicate the position of the posterior-most portion of the implant 10. Spinal fusion implant 10 may include at least one radiographic marker positioned at the intersection of the second lateral side 18 and the distal end 22. Preferably, there are two markers positioned at this intersection, a first radiographic marker 28 extending at least partially through the implant from the top surface 12 and radiographic marker 30 extending at least partially through the implant from bottom surface 14 to identify the tallest points of the spinal fusion implant 10. The distal end 22 may be provided with radiographic marker 32 comprising a unitary element fully extending between the top and bottom surfaces 12, 14 at or near the intersection of distal end 22 and first lateral side 16. Radiographic marker 32 may preferably indicate the position of the anterior-most portion of the spinal fusion implant as well as an indication of the anterior height of the implant. As will be shown in greater detail below, the orientation of radiographic markers 26, 28, 30, 32 provide an indication of the oblique placement of the spinal fusion implant 10 and the direction of rotation that is needed to bring the implant 10 into the desired positioning.

The spinal fusion implant 10 includes a large aperture 34 extending between top and bottom surfaces 12, 14. FIGS. 1-4 illustrate aperture 34 extending in a vertical fashion between the top and bottom surfaces 12, 14. The aperture 34 may be provided in any number of suitable shapes, including but not limited to generally circular, generally triangular and/or generally oblong (as shown by example in FIGS. 3 and 4). This single aperture 34 is an additional feature for promoting fusion between the upper and lower vertebral bodies which allow a boney bridge to form through the spinal fusion implant 10.

According to another further aspect of the present invention, this fusion may be facilitated or augmented by including osteoinductive material(s) within the aperture 34 and/or adjacent to the spinal fusion implant 10. Such osteoinductive materials may be introduced before, during, or after insertion of the spinal fusion implant 10 of the present invention, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D, L-lactide-co-glycolide) based polymers, such as those disclosed in U.S. Pat. No. 6,013,853.

Figure 5:
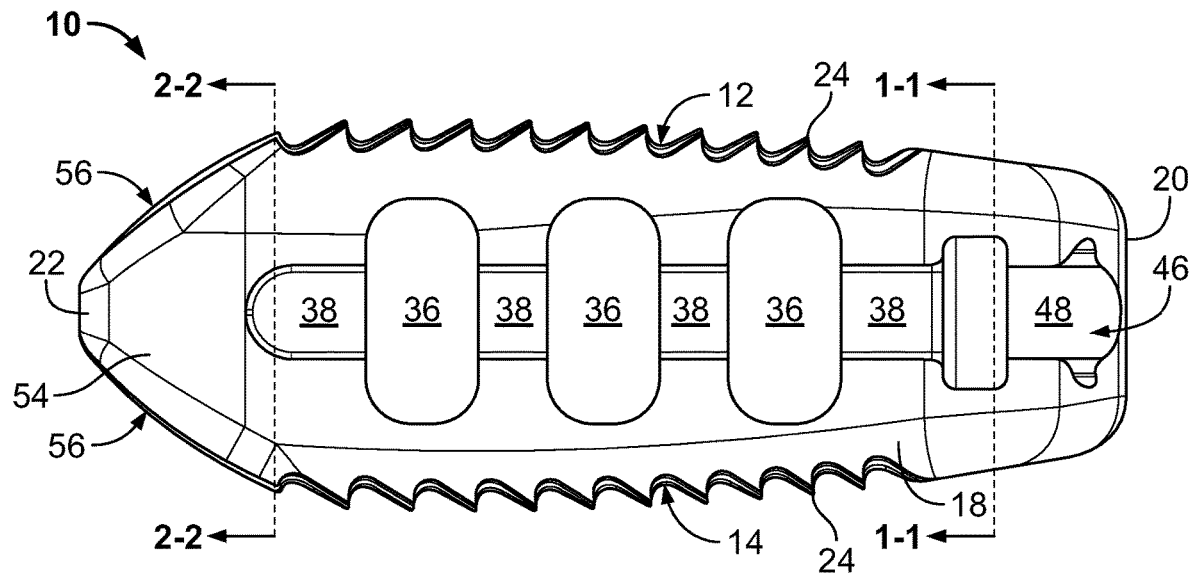
FIG. 5 is a first side view of the spinal fusion implant of FIG. 1.
Figure 6:
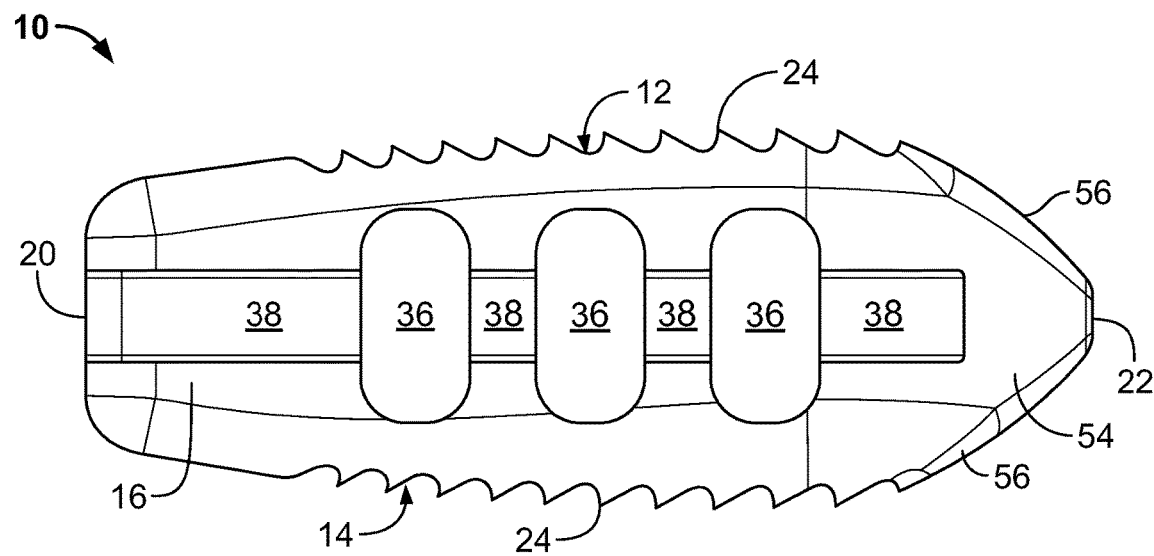
FIG. 6 is a second side view of the spinal fusion implant of FIG. 1.

FIGS. 5-6 depict the spinal fusion implant 10 from side views. First and second lateral sides 16, 18 are generally parallel to one another (shown best in FIGS. 3-4). The spinal fusion implant 10 may be further provided with one or more lateral apertures 36 extending generally perpendicularly therethrough from one lateral side 16 to the other 18. Lateral apertures 36 function to provide visualization at the time of implantation and at subsequent clinical evaluations. Lateral apertures 36 may be provided in any of a variety of suitable shapes, including but not limited to generally circular, generally triangular, generally rectangular, and/or generally oblong (shown by example in FIG. 5-6), or any combination thereof. Although the spinal fusion implant 10 herein includes a pair of lateral apertures 36, the spinal fusion implant 10 may include any number of lateral apertures 36 as desired.

Based on the generally radiolucent nature of the implant 10, the lateral apertures 36 provide the ability to visualize the interior of the implant 10 during X-ray and/or other suitable imaging techniques which are undertaken from the lateral (or "side") perspective of the implant 10. If fusion has taken place, the lateral apertures 36 will provide a method for the surgeon to make follow up assessments as to the degree of fusion without any visual interference from the spinal fusion implant 10. Further, the lateral apertures 36 will provide an avenue for cellular migration to the exterior of the spinal fusion implant 10. Thus the spinal fusion implant 10 will serve as additional scaffolding for bone fusion on the exterior of the spinal fusion implant 10.

The spinal fusion implant 10 further includes slots 38 extending from proximal surface 40 along first and second lateral sides 16, 18. Slots 38 are sized and dimensioned to interface with distal insertion tangs 122 on insertion instrument 100 to provide steerability and torsional support during insertion and insert-and-rotate maneuvers as will be described in greater detail below.

FIG. 7 illustrates the proximal end 20 of the spinal fusion implant 10 of the present invention. The proximal end 20 has a proximal surface 40 that is tapered (angled) from the first lateral surface 16 to the second lateral surface 18. This angular surface provides an advantage by allowing an oblique positioning of the spinal fusion implant 10 within the intervertebral space, without protruding into the spinal canal to avoid dural impingement after insertion. Additionally, the tapered nature of the proximal surface 40 can aid in overall fit of the spinal fusion implant 10 within the vertebral disc space. Significantly, the tapered proximal surface 40 on the proximal end 20 enables the spinal fusion implant 10 to maximize contact with the posterior portion of the cortical ring of each adjacent vertebral body.

The proximal end 20 may include a proximal engagement recess 46 which extends inwardly in a generally perpendicular fashion relative to the proximal end 20. Although shown as having a generally semi-circular cross-section, it will be appreciated that the proximal engagement recess 46 may be provided having any number of suitable shapes or cross-sections, including but not limited to circular or triangular. Furthermore, the proximal engagement recess 46 may extend fully or at least partially along the length of the proximal surface 40. Proximal engagement recess 46 is dimensioned to receive and engage with an insertion tool (described below) for inserting the spinal fusion implant 10 into the intervertebral space.

Figure 8:
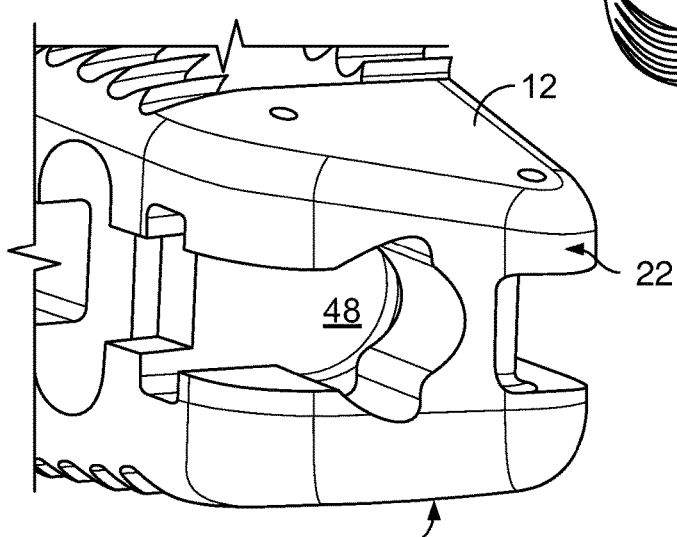
FIG. 8 is a detailed perspective view the proximal end of the spinal fusion implant of FIG. 1.
Figure 9:
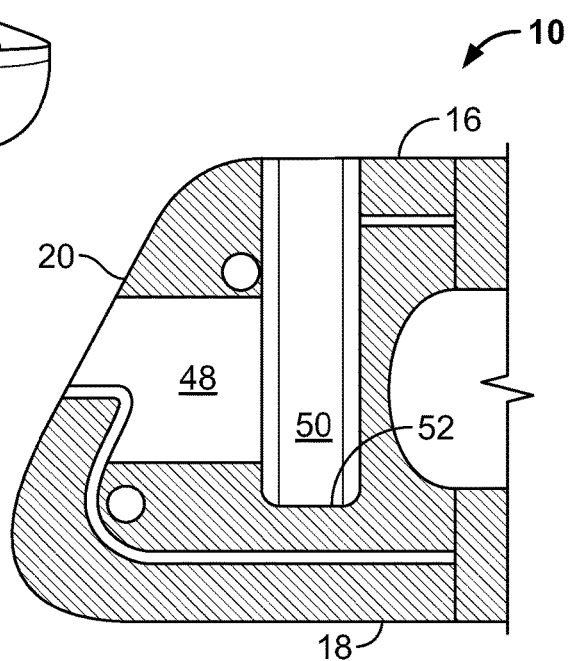
FIG. 9 is a detailed cross-section view of the proximal end of the spinal fusion implant of FIG. 1.

According to the embodiment shown (by way of example only in FIGS. 7-9), the proximal engagement recess 46 is comprised of a keyed insertion slot 48, a locking recess (undercut) 50, and a locking wall 54. Keyed insertion slot 48 is complementary in shape to the rotational lock 128 on the inner shaft 108. When the rotational lock 128 is inserted into the keyed insertion slot 48, it falls into the locking recess 50 (or undercut) after it rotates) and abuts locking wall 52, thereby locking the spinal fusion implant 10 with insertion instrument 100 and preventing the implant 10 and insertion instrument 100 from moving relative to one another.

FIG. 10 illustrates the distal end 22 of the spinal fusion implant 10 of the present invention. The distal end 22 has a conical (bullet-shaped) distal nose including a pair of first tapered (angled) surfaces 54 and a pair of second tapered (angled) surfaces 56. First tapered surfaces 54 extend between lateral surfaces 16, 18 and the distal end 22. First tapered surface 54 extending from second lateral surface/side 18 is generously curved between distal nose and lateral side 18 and functions to distract the vertebrae adjacent to the target intervertebral space during insertion of the spinal fusion implant 10. According to the embodiment shown, the distal end 22 is asymmetrically positioned relative to the longitudinal axis of the implant. Specifically, the distal end is preferentially curved (curved surface 44) towards the second lateral side 18. The asymmetric distal end 22 facilitates insertion while providing maximal surface area of the spinal fusion implant 10. The asymmetric distal end 22 provides a gradual lead-in taper which protects nervous tissue in the spinal canal when placing the spinal fusion implant 10 into the disc space on its side and utilizing the insert-and-rotate technique. Once implanted and rotated, the asymmetrical distal end 22 provides increased structural support by approximating the anatomical shape of the anterior portion of the cortical ring of each adjacent vertebral body.

The top and bottom surfaces 12, 14 may be angled or tapered from distal (anterior end) 22 to proximal (posterior) end 20. According to an example embodiment, in which the implant 10 has a variable height tapering in a direction oblique to the length and width of the implant, as measured by the distance between the top and bottom surfaces 12, 14. Because the variable height of the implant tapers in a direction oblique to the length of the implant, the height of the implant at the distal end 22 is greater than the height of the proximal end 20. Because the direction in which the height of the implant tapers is also oblique to the width of the implant, the height of the first lateral side 16 differs from the height of the second lateral side 18 along at least a portion of the length of the implant. The practical result of this tapering along a direction oblique to the length and width of the implant is that when the spinal fusion implant 10 is inserted obliquely within the disc space, the effective height correction occurs generally parallel to the sagittal plane (i.e. anterior to posterior). This provides for optimal restoration of the natural lordotic curvature of the lumbar spine. By way of example only, the oblique tapering of the implant 10 height may occur at an angle measuring from 5 to 15 degrees.

Figure 11:
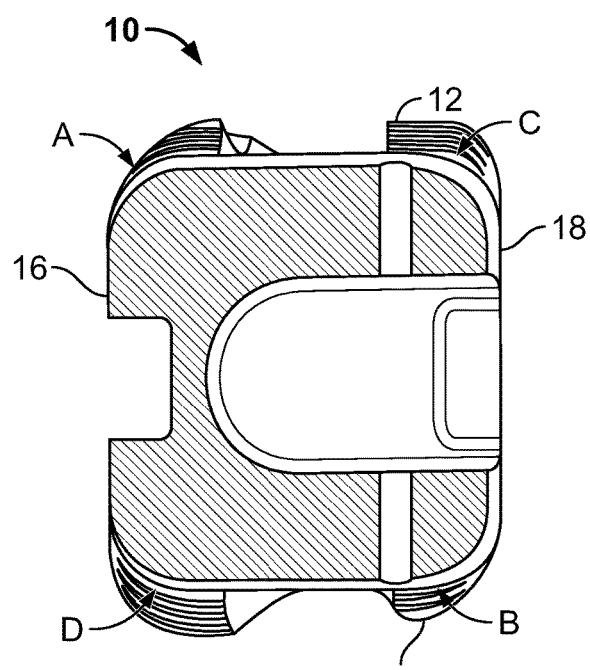
FIG. 11 is a cross-section view of the proximal end of the spinal fusion implant of FIG. 1 taken along the line 1-1.
Figure 12:
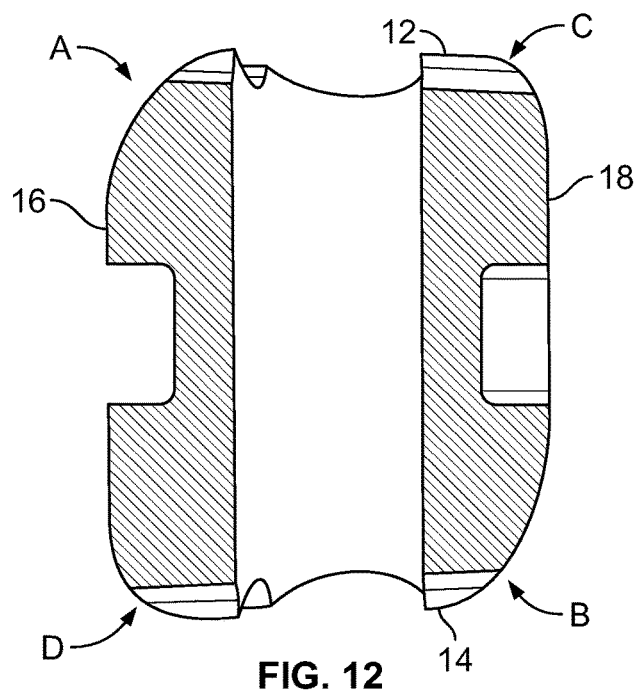
FIG. 12 is a cross-section view of the distal end of the spinal fusion implant of FIG. 1 taken along the line 2-2.
Figure 13:
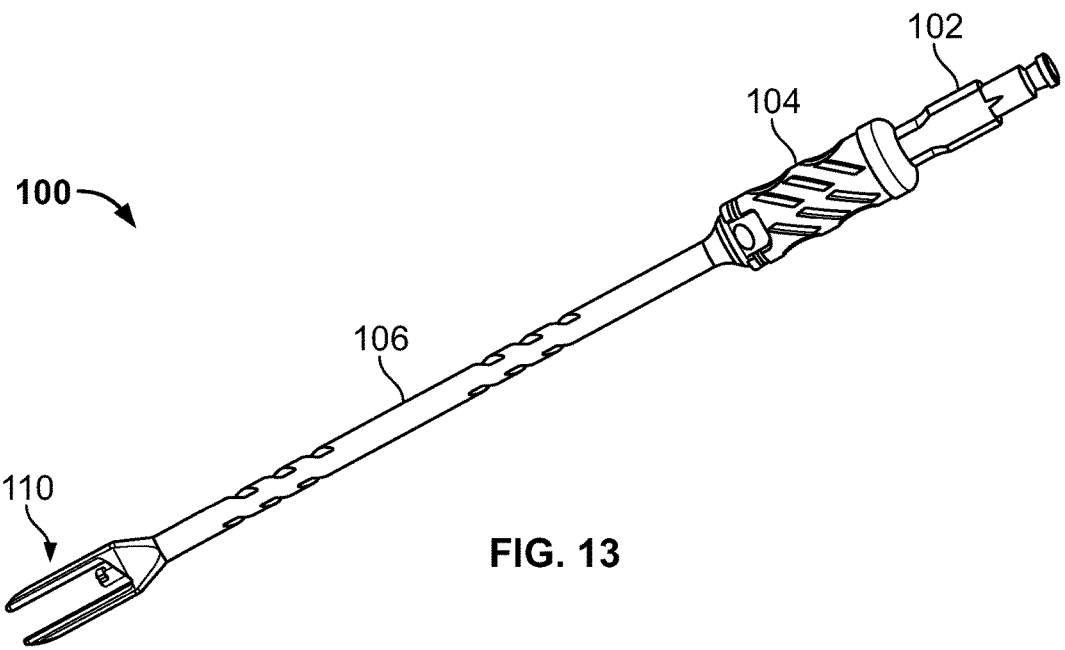
FIG. 13 is a perspective view of an insertion instrument according to one embodiment of the present invention.
Figure 14:
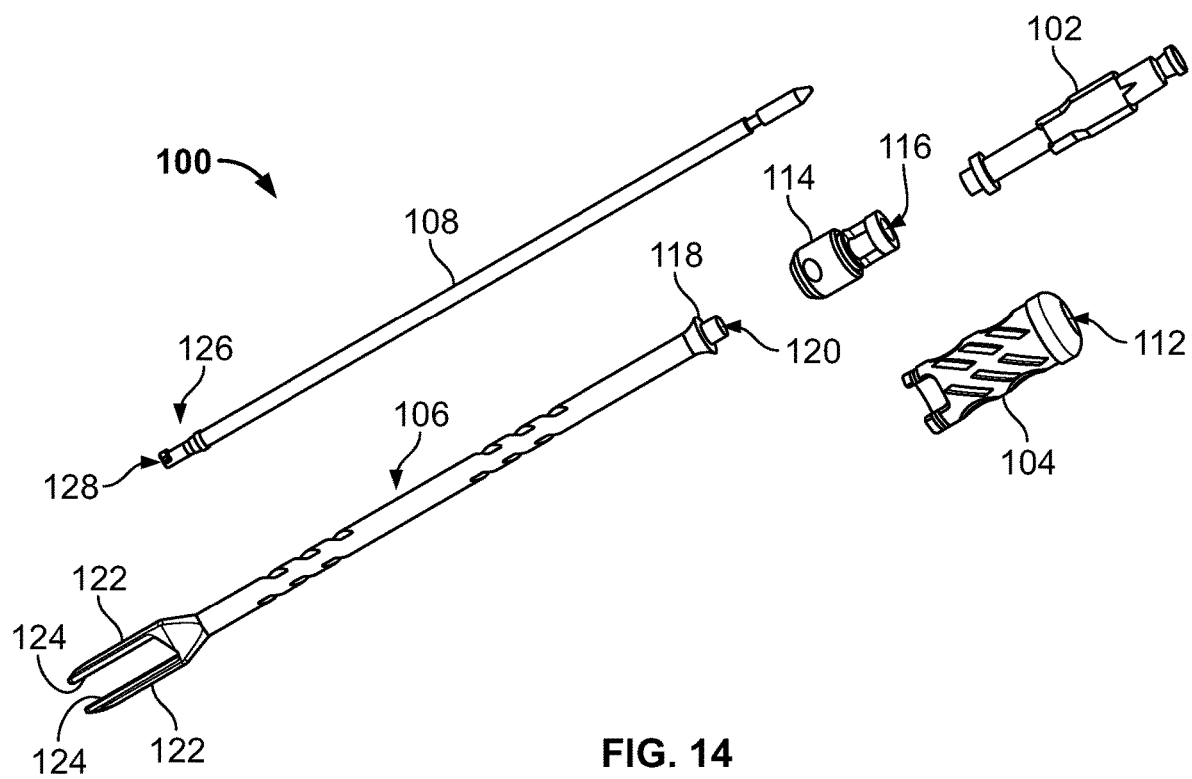
FIG. 14 is an exploded perspective view of the insertion instrument of FIG. 13.

The spinal fusion implant 10 preferably has variable rounds on opposing corners of the implant 10 when looking at the implant along its longitudinal axis. These opposing-corner variable rounds (shown here as Rounds A and B) vary in their radius along the length of the implant. In the embodiment shown in FIGS. 11-12, Rounds A-B have a larger radius at the distal end 22 and a smaller radius at the proximal end 20. Smaller rounds (shown here as Rounds C and D) have constant and equal radii along the length of the spinal fusion implant. The radii at Rounds A and B are preferably approximately equal at any given cross-section along the entire length of the spinal fusion implant 10. These opposing-corner variable rounds allow for more gradual lead-in at the distal end 22 which facilitates insertion of the spinal fusion implant 10 during insert and rotate maneuvers.

The spinal fusion implant may be further provided with asymmetric convex top and bottom surfaces between first and second lateral sides to approximate the anatomical concavities of the inferior endplate of the superior vertebra and the superior endplate of the inferior vertebra. According to one embodiment, the radius of curvature between first and second lateral sides 16, 18 is preferably smaller for the top surface 12 than the bottom surface 14 the curvature of the top surface 12 will be different at every cross-section along the length of the spinal fusion implant 10 than the curvature of the bottom surface 14. It is well-known that vertebral body endplates generally have some degree of concavity, however the concavity of adjacent endplates within an intervertebral disc space are rarely identical. The degree of convexity of the top and bottom surfaces 12, 14 between first and second lateral sides 16, 18 is not identical to account for the asymmetrical concavity of the inferior endplate of the superior vertebral body and the superior endplate of the inferior body. According to a preferred embodiment, the top surface 12 has a larger degree of convexity between first and second lateral sides 16, 18 than bottom surface 14.

It can be appreciated by one skilled in the art that the top and bottom surfaces 12, 14 may be configured in any number of suitable shapes to better match the natural contours of the vertebral end plates. For example, top and bottom surfaces 12, 14 may be generally planar, generally concave, and/or generally convex. According to one or more preferred embodiments, the top surface 12 of the spinal fusion implant 10 is convex to approximate the concave of the inferior endplates of the superior vertebral body and the bottom surface 14 of the spinal fusion implant is concave to approximate the concave surface of the superior endplates of the inferior vertebral body. The degree of convexity of the top and bottom surfaces 12, 14 along the length of the implant between proximal and distal ends 20, 22 is not identical to account for the asymmetrical concavity of the inferior endplate of the superior vertebral body and the superior endplate of the inferior vertebral body. According to one or more preferred embodiments, the top surface 12 has a greater amount of convexity than bottom surface 14 along the length of the implant.

The spinal fusion implant 10 may be introduced into a spinal target site through use of any of a variety of suitable surgical instruments having the capability to engage the implant. As described in FIGS. 13-16, the present invention includes an insertion instrument 100 for implanting the spinal fusion implant 10. According to a broad aspect, the insertion instrument includes a proximal connection region 102, a thumbwheel 104, an outer shaft 106, an inner shaft 108, and a distal insertion region 110.

Figure 15:
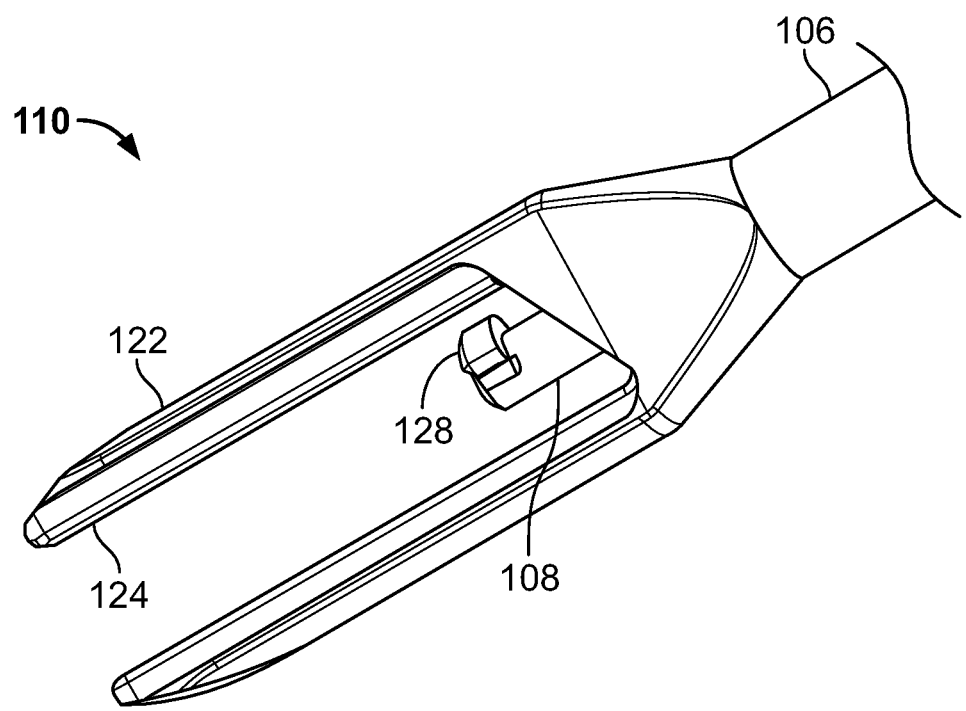
FIG. 15 is a detailed perspective view of the distal end of the insertion instrument of FIG. 13.
Figure 16:
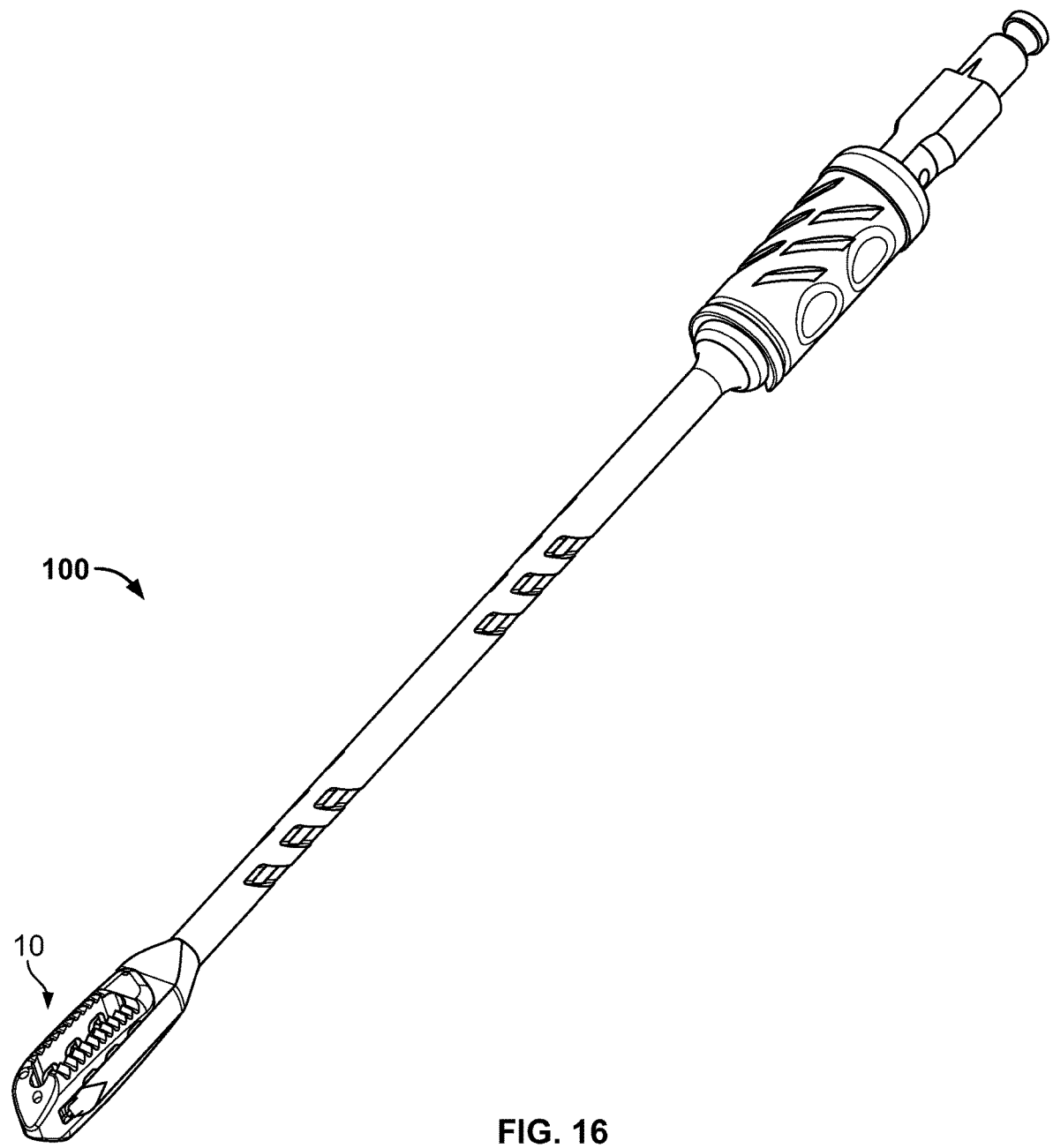
FIG. 16 is a perspective view of the insertion instrument of FIG. 13 coupled to the spinal fusion implant of FIG. 1.
Figure 17:
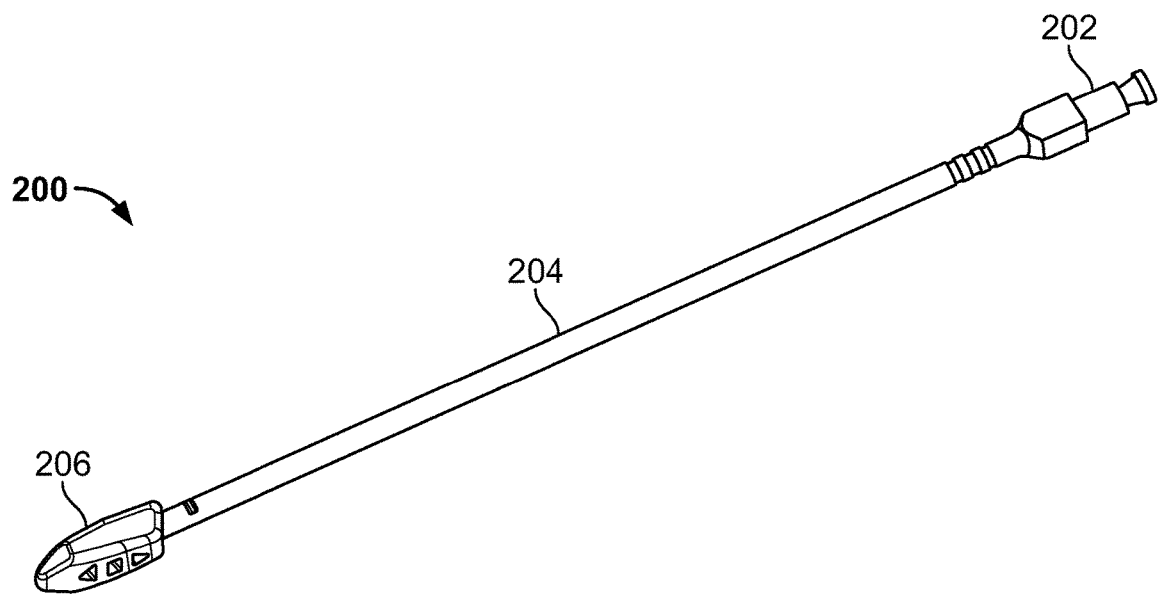
FIG. 17 is a perspective view of an implant trial instrument according to one embodiment of the present invention.
Figure 18:
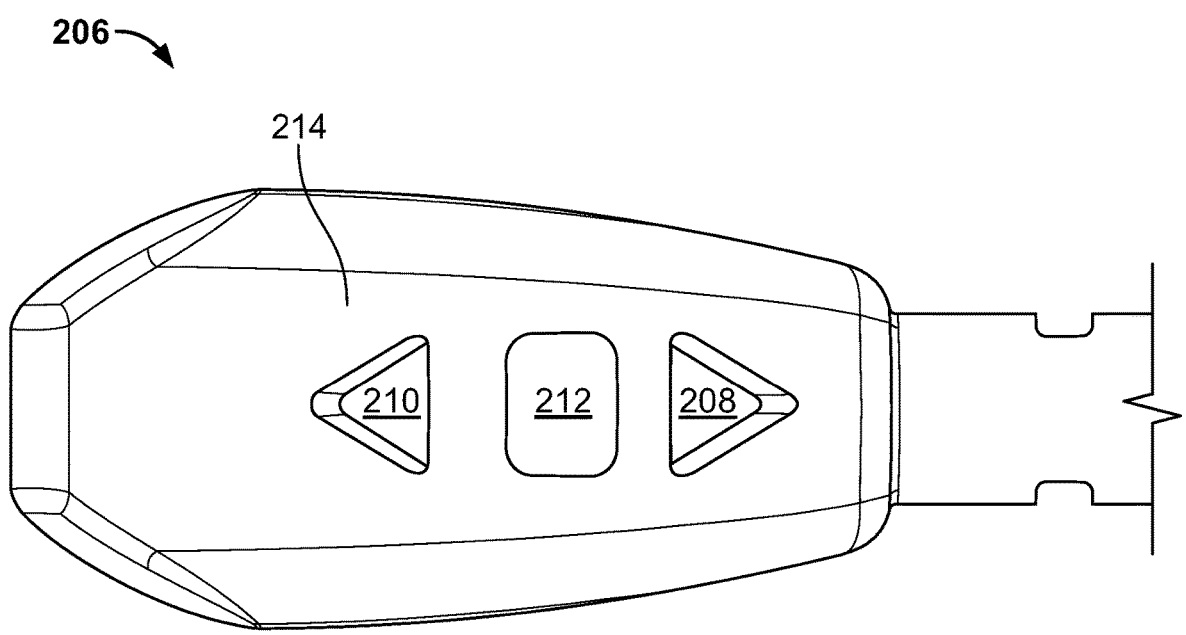
FIG. 18 is a side view of the distal head of the trial instrument of FIG. 17 in a first orientation.

The proximal connection region 102 is sized and dimensioned for attaching and/or detaching a handle (not shown). The thumbwheel 104 contains an inner aperture 112 for housing an interior spring (not shown) and a lock 114. Lock 114 resides at least partially within thumbwheel 104 and includes an aperture 116 and is rotatable between locked and unlocked positions via thumbwheel 104 as will be described in greater detail below. Outer shaft 106 includes a proximal end 118 extending distally from the thumbwheel 104, a central elongate bore 120 carrying the inner shaft 108 therethrough, and distal insertion tangs 122. Distal insertion tangs 122 engage with the slots 38 of the spinal fusion implant 10 via insertion slides 124 as will be explained in greater detail below. The inner shaft 108 includes a distal region 128 which terminates in a rotational locking mechanism. As shown in FIG. 15, according to one embodiment, rotational lock 128 includes a half-moon shaped key that is sized and dimensioned to fit into keyed insertion slot 48.

The insertion instrument 100 is attached to the spinal fusion implant 10 by aligning the distal insertion tangs 122 with slots 38 on first and second lateral sides 16, 18. The implant may be attached to the positioning insertion slides 124 into the slots 38 until the positioning insertion tangs 122 are fully inserted within the spinal fusion implant 10 and keyed rotational lock 128 is inserted into keyed insertion slot 48 on the proximal end 20 of the spinal fusion implant 10. Pushing the spring-loaded thumbwheel 104 slightly and spinning it to the right moves the lock from the unlocked position to the locked position. As the thumbwheel 104 moves, the rotational lock rotates 180 degrees and it falls into the locking recess 50 (or undercut) and abuts locking wall 52. Thus, the rotational lock 128 prevents the implant 10 from moving in an axial direction while the distal insertion tangs 122 prevent translation in the medial/lateral and cranial/caudal directions thereby locking the spinal fusion implant 10 with insertion instrument 100 and preventing the implant 10 and insertion instrument 100 from moving relative to one another.

The spinal fusion implant 10 may be introduced into a spinal target site having first been prepared through the use of one or more trial instruments having the capability to size the spinal target site. As described in FIGS. 17-20, the present invention a trial instrument for selecting the proper size of spinal fusion implant 10 and determining the correct position of the spinal fusion implant 10 under fluoroscopy prior to insertion. The trial instrument 200 comprises a connector portion 202, a shaft portion 204, and a trial head 206. The trial head 206 has a size and shape of the spinal fusion implant 10 to be used. The trial head 200 has a series of windows 208, 210, 212 formed within lateral sides 214. Each window 208, 210, 212 preferably extends generally perpendicularly from one lateral side 214 of the trial head 206 to the other.

The trial instrument 200 may be formed of any material that prevents the passage of x-rays therethrough (e.g. titanium). Since the windows extend completely through the trial head 206, the x-rays are able to pass through and both the size and shape of the windows 208, 210, 212 are discernable under fluoroscopy. In the example shown here, the trial head 206 is provided with three windows, however any number may be used. By way of example, the trial head 206 has a proximal shaped window 208, a distal shaped window 210, and a central shaped window 212. The shaped windows 208, 210, 212 are arranged linearly along the axis of the trial inserter 20. The central window 212 is shown as having a generally rectangular shape, however other shapes are possible. The central window 212 comprises an aperture having a longitudinal axis that is perpendicular to the longitudinal axis of the trial inserter 200. The proximal and distal shaped windows are positioned on either side (proximal side and distal side, respectively) of the central window 212. By way of example, the proximal shaped window 208 has a generally triangular shape and is arranged to "point" in a proximal direction. The distal shaped window 210 also has a generally triangular shape and is arranged to "point" in a distal direction. The proximal and distal shaped windows 208, 210 comprise apertures having co-planar non-parallel longitudinal axes.

When viewed from the correct side, the axes of the proximal and distal shaped windows 208, 210 are divergent from one another and the central axis. This allows for rapid visual determination of rotational positioning of the trial head 206, and also for immediate instruction on how to correct improper positioning. The parallax distortion of the fluoroscopic image is minimal when the trial head 206 is centered within the image and therefore the x-rays travel within a directly parallel manner. Because metal prevents the passage of x-rays, a window will appear smaller if it is not directly aligned with the direction of the x-rays. As a result, one window (e.g. the central shaped window 212) is an indicator of directly parallel alignment), one window (e.g. the distal shaped window 208) is an indicator of "hyper-obliqueness" and one window (e.g. the proximal shaped window 210) is an indicator of hypo-obliqueness."

Figure 19:
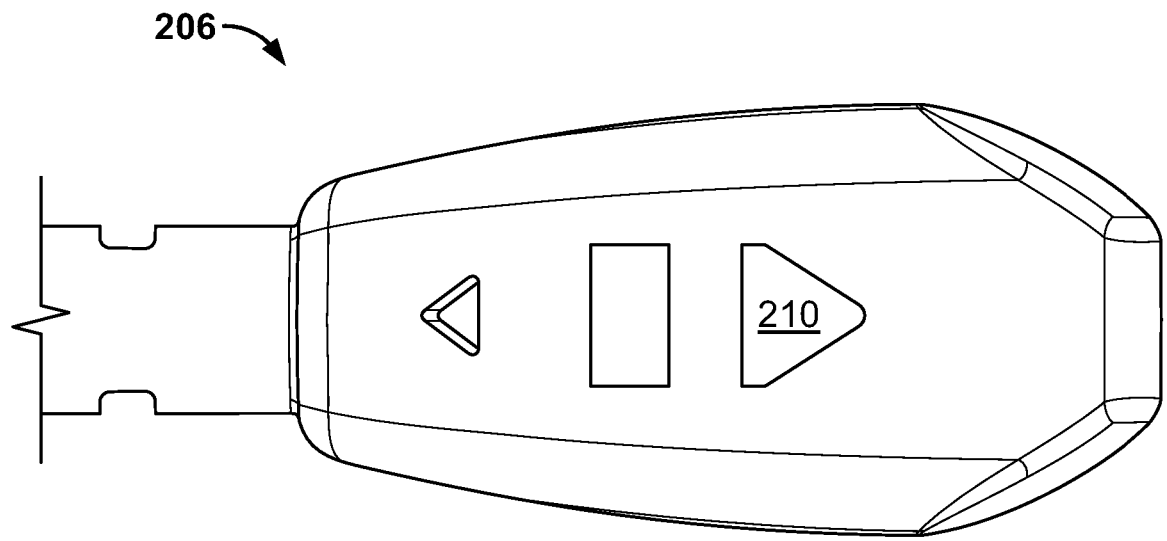
FIG. 19 is a side view of the distal head of the trial instrument of FIG. 17 in a second orientation.
Figure 20:
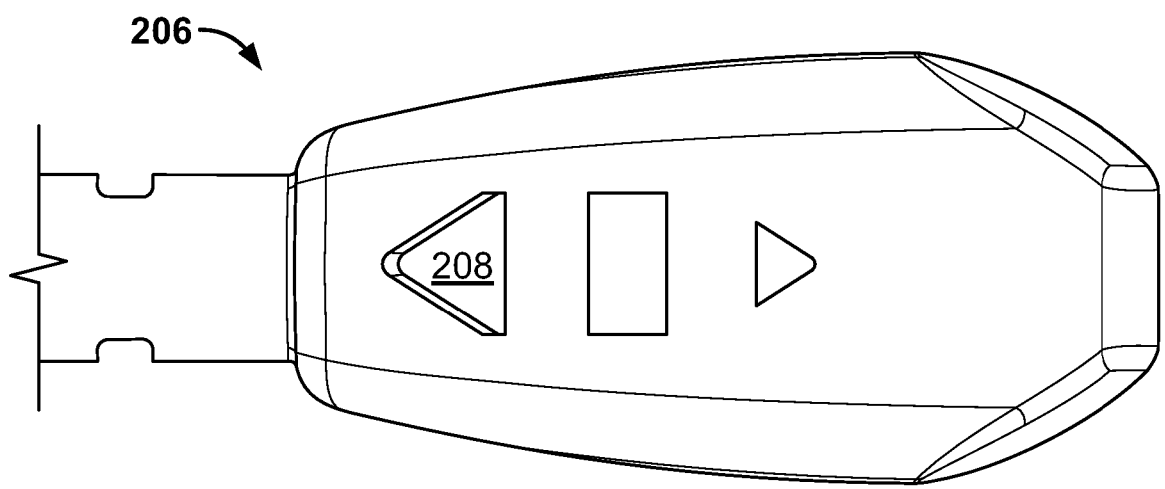
FIG. 20 is a side view of the distal head of the trial instrument of FIG. 17 in a third orientation.

Because the user immediately knows whether the trial instrument 200 is "hyper-oblique" or "hypo-oblique", he/she also immediately knows the direction to move his/her hand to get the correct placement of the trial head 206, thereby decreasing the need for trial inserter repositioning and localizing x-rays thus reducing x-ray fluoroscopic exposure for user and patient. By way of example, when a trial instrument 200 is inserted directly oblique (proper position), the proximal and distal shaped windows 208, 210 will appear the same size under fluoroscopy. However when one of the proximal and distal shaped windows 208, 210 is larger than the other, the surgeon/user knows that the trial is not correctly positioned. Pivoting the trial head 206 in the direction of the larger window, the desired position may be achieved. FIG. 19 is an example of a "hyper-oblique" trial head 206. In this instance, the distal shaped window 210 is larger than the proximal shaped window 208, indicating suboptimal positioning of the trial 200. Pivoting the trial 200 in the direction of the distal shaped window 210 will bring the trial head 206 into ideal trial positioning. FIG. 20 is an example of a "hypo-oblique" trial head 206. In this instance, the proximal shaped window 208 is larger than the distal shaped window 210, also indicating suboptimal positioning in the trial 200. Pivoting the trial 200 in the direction of the proximal shaped window 208 will bring the trial head 206 into ideal trial positioning.

According to a broad aspect of the present invention, the spinal fusion implant 10 is capable of being used in minimally invasive surgical procedures, needing only a relatively small operative corridor for insertion. By way of example only, the spinal fusion implant 10 will now be described in relation to a transforaminal lumbar interbody fusion (TLIF) technique, in which the intervertebral disc space is approached from a postero-lateral direction, however it should be understood that the spinal fusion implant 10 is capable of use in a variety of surgical procedures not described herein. After creation of this operative corridor and preparing the disc space (using techniques commonly known and used in the art), a trial inserter (e.g. the trial inserter of FIGS. 17-20) may be used to select the proper size of the spinal fusion implant 10.

The spinal fusion implant 10 is mated to an insertion device (e.g. insertion instrument 100) and advanced through the operative corridor toward the target intervertebral space. The spinal fusion implant 10 may be oriented with the lateral sides 16, 18 facing in a caudad/cephalad direction, for example with the first lateral side 16 facing a caudad (inferior) direction and the second lateral side 18 facing a cephalad (superior) direction. When the distal end 22 of the implant 10 reaches the intervertebral disc space, each of the pair of first tapered surfaces 54 will come into contact with one of the adjacent vertebral bodies. As the implant 10 is advanced into the intervertebral disc space, the pair of first tapered surfaces 54 will serve to distract the vertebral bodies, allowing the implant to fully enter the intervertebral space.

Since the first and second lateral sides 16, 18 are preferably provided with generally smooth surfaces, the spinal fusion implant 10 should advance with relative ease into the disc space once the adjacent vertebral bodies have been distracted. Once the implant 10 has been positioned in its desired location, the user will then rotate the implant 90° such that the top and bottom surfaces 12, 14 face in a caudad/cephalad direction and the anti-migration features 24 engage the vertebral bodies. Significantly, the direction of rotation is critical to ensure proper placement of the implant 10 such that the edges of the proximal surface 40 rest on the cortical ring of the vertebral bodies, that the proximal surface 40 does not protrude into the spinal canal, and the implant 10 tapers in the appropriate direction (e.g. anterior to posterior rather than posterior to anterior). For example, if the spinal fusion implant 10 approaches a patient's spine posteriorly from the right with the (longer) first lateral side 16 facing caudally, then implant 10 must be rotated in a counter-clockwise direction to achieve proper positioning. Similarly, if the spinal fusion implant 10 approaches a patient's spine posteriorly from the left side with the (longer) first lateral side 16 facing caudally, then implant 10 must be rotated in a clockwise direction to achieve proper positioning. According to one embodiment the implant may include one or more markings or other indicia to help facilitate the proper positioning. According to one embodiment (not shown), for example, the first lateral side 16 may be marked with "lateral" to indicate that it should face to the exterior of the disc space, and the second lateral side 17 may be marked with "medial" to indicate that it should face the interior of the disc space when the implant 10 is rotated into position. Once the spinal fusion implant 10 has been rotated into position, the insertion instrument 100 may be detached and removed from the operative corridor.

Figure 21A:
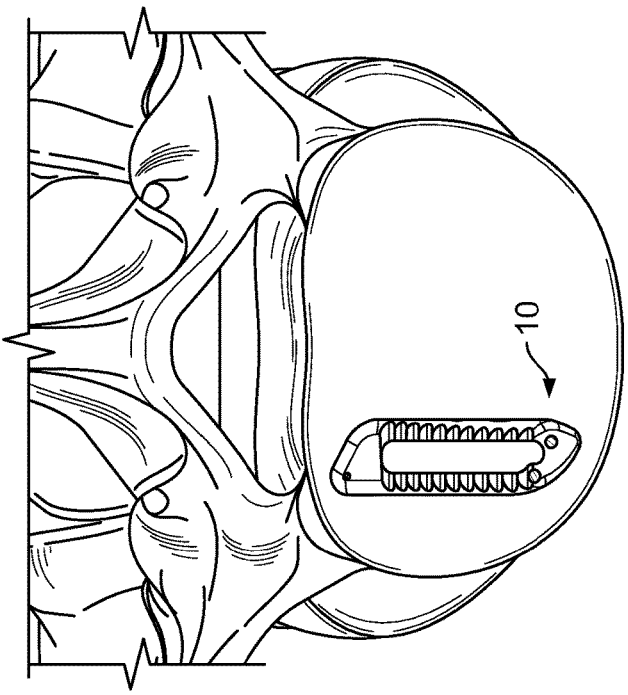
FIG. 21 A is a top plan view of an example of a spinal fusion implant inserted into an intervertebral disc space but not placed in a desired oblique configuration.
Figure 22A:
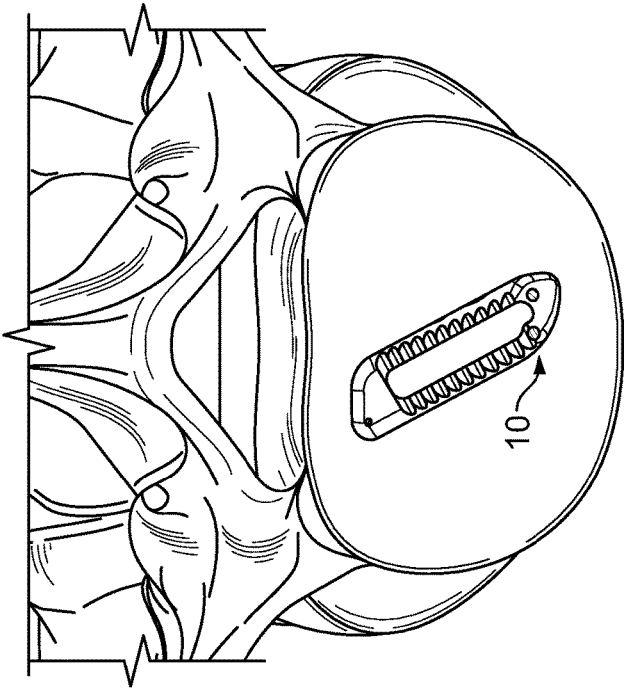
FIG. 22 A is a top plan view of an example of a spinal fusion implant inserted into an intervertebral disc space placed in a desired oblique configuration.
Figure 21B:
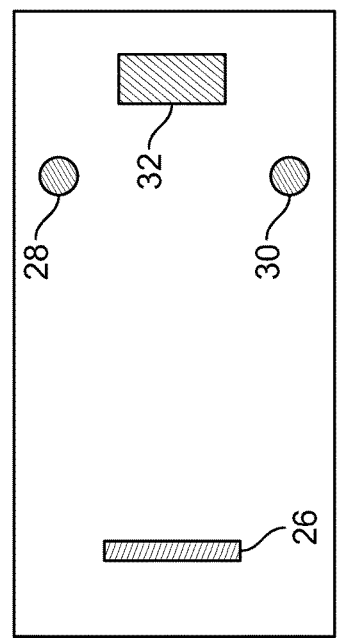
Figure 22B:
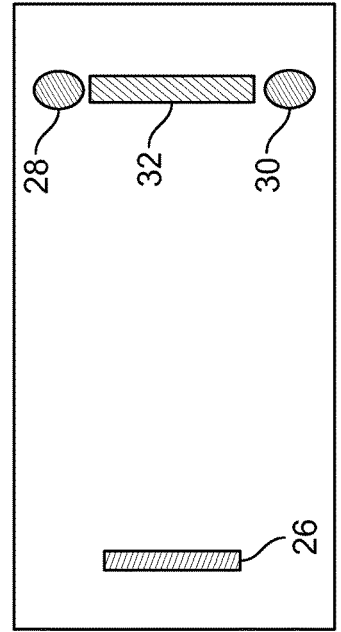

In accordance with the present invention, the user is provided with one or more methods to aid in verifying the desired positioning of the spinal fusion implant 10 using lateral fluoroscopy to localize internal visualization markers and verify movement of the spinal fusion implant 10 within the disc space. FIG. 21 A depicts a spinal fusion implant 10 positioned in the intervertebral disc space, however not in the desired oblique alignment. As illustrated in FIG. 21 B, radiographic markers 28, 30 will appear spaced apart from radiographic marker 32 on lateral fluoroscopy. FIG. 22 A depicts a spinal fusion implant 10 positioned in the intervertebral disc space, in the desired oblique alignment. As illustrated in FIG. 22 B, radiographic markers 32 will appear to align with radiographic marker 32 on lateral fluoroscopy.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An inserter for implanting a spinal implant, the inserter comprising:
    an outer shaft comprising a central bore, a proximal end, a distal end, and one or more insertion tangs at the distal end thereof;
    an inner shaft running through the central bore of the outer shaft, the inner shaft comprising a rotational lock at a distal end thereof, the rotational lock including a key that is shaped and sized to fit into a keyed insertion slot of the spinal implant;
    a thumbwheel coupled to the proximal end of the outer shaft, the thumbwheel being configured to translate and to rotate the inner shaft relative to the outer shaft, thereby locking or unlocking the spinal implant to the inserter,
        wherein the thumbwheel comprises a housing and an inner aperture extending longitudinally within the housing, and a proximal connection member configured to extend proximally from the thumbwheel; and a lock disposed at least partially within the inner aperture of the thumbwheel, wherein the lock includes an aperture extending longitudinally therein, the aperture having a first end configured to couple to a proximal end of the inner shaft and a second end configured to couple to the proximal connection member, wherein the inserter is configured to insert the spinal implant, in a locked configuration, with the one or more insertion tangs facing an inferior or a superior direction, wherein, in an unlocked configuration, the key is in a first position, and wherein, in the locked configuration, the key is in a second position rotated 180° relative to the first position.

2. The inserter of claim 1, wherein, in the locked configuration, the rotational lock prevents movement of the spinal implant in a proximal-to-distal direction and the one or more insertion tangs prevent movement of the spinal implant in a medial-to-lateral direction and a superior-to-inferior direction, thereby locking the spinal implant to the inserter.

3. The inserter of claim 1, wherein in the locked configuration, the key is configured to abut an undercut within the spinal implant such that the key is prohibited from being removed from the keyed insertion slot.

4. The inserter of claim 1, wherein the key is asymmetric about at least one axis, and
wherein the key, in the locked configuration, is configured to enter the keyed insertion slot, fall into a locking recess that is distal to the keyed insertion slot, and abut a locking wall of the spinal implant.

5. The inserter of claim 1, wherein the keyed insertion slot comprises a size and shape that is complementary to a size and shape of the key.

6. The inserter of claim 1, wherein the one or more tangs extends further in a distal direction than the rotational lock.

7. The inserter of claim 1, wherein the proximal connection member is further configured to removably couple to a handle.

8. The inserter of claim 1, wherein each of the one or more insertion tangs comprises an insertion slide configured to slideably engage with a lateral slot of the spinal implant.

9. An inserter for implanting a spinal implant, the inserter comprising:
an outer shaft comprising a central bore, a proximal end, a distal end, and one or more insertion tangs at the distal end thereof;
an inner shaft running through the central bore of the outer shaft, the inner shaft comprising a rotational lock at a distal end thereof;
a thumbwheel coupled to the proximal end of the outer shaft, the thumbwheel being configured to translate and rotate the inner shaft relative to the outer shaft, thereby locking or unlocking the spinal implant to the inserter,
wherein the thumbwheel comprises a housing and an inner aperture extending longitudinally within the housing;
a proximal connection member configured to extend proximally from the thumbwheel; and
a lock disposed at least partially within the inner aperture of the thumbwheel,
wherein the lock includes an aperture extending longitudinally therein, the aperture having a first end configured to couple to a proximal end of the inner shaft and a second end configured to couple to the proximal connection member, wherein the rotational lock comprises a key that is shaped and sized to fit into a keyed insertion slot of the spinal implant, and the key is asymmetric about at least one axis, wherein, in an unlocked position, the key is in a first position, and wherein, in a locked configuration, the key is in a second position 180° relative to the first position.

10. The inserter of claim 9, wherein, in the locked configuration, the rotational lock prevents movement of the spinal implant in a proximal-to-distal direction and the one or more insertion tangs prevent movement of the spinal implant in a medial-to-lateral direction and a superior-to-inferior direction, thereby locking the spinal implant to the inserter.

11. The inserter of claim 9, wherein the key is half-moon shaped.

12. The inserter of claim 9, wherein the key, in the locked configuration, is configured to enter the keyed insertion slot, fall into a locking recess that is distal to the keyed insertion slot, and abut a locking wall of the spinal implant.

13. The inserter of claim 9, wherein the keyed insertion slot comprises a size and shape that is complementary to a size and shape of the key.

14. The inserter of claim 9, wherein the one or more tangs extends further in a distal direction than the rotational lock.

15. The inserter of claim 9, further comprising a proximal connection member configured to extend proximally from the thumbwheel, wherein the proximal connection member is further configured to removably couple to a handle.

16. The inserter of claim 9, wherein each of the one or more insertion tangs comprises an insertion slide configured to slideably engage with a lateral slot of the spinal implant.

17. The inserter of claim 9, wherein the inserter is configured to insert the spinal implant, in a locked configuration, with the one or more insertion tangs facing an inferior or a superior direction.

18. An inserter for implanting a spinal implant, the inserter comprising:
an outer shaft comprising a central bore, a proximal end, a distal end, and one or more insertion tangs at the distal end thereof;
an inner shaft running through the central bore of the outer shaft, the inner shaft comprising a rotational lock at a distal end thereof;
a thumbwheel coupled to the proximal end of the outer shaft, the thumbwheel being configured to translate and to rotate the inner shaft relative to the outer shaft, thereby locking or unlocking the spinal implant to the inserter,
wherein the thumbwheel comprises a housing and an inner aperture extending longitudinally within the housing;
a proximal connection member configured to extend proximally from the thumbwheel; and
a lock disposed at least partially within the inner aperture of the thumbwheel, wherein the lock includes an aperture extending longitudinally therein, the aperture having a first end configured to couple to a proximal end of the inner shaft and a second end configured to couple to the proximal connection member, wherein, in an unlocked configuration, the rotational lock is in a first position, wherein, in a locked configuration, the rotational lock is in a second position rotated 180° relative to the first position, wherein, in the locked configuration, the rotational lock prevents movement of the spinal implant in a proximal-to-distal direction and the one or more insertion tangs prevent movement of the spinal implant in a medial-to-lateral direction and a superior-to-inferior direction, and the rotational lock abuts an undercut proximate to the keyed insertion slot in the spinal implant, thereby locking the spinal implant to the inserter, and wherein the inserter is configured to insert the spinal implant, in a locked configuration, with the one or more insertion tangs facing an inferior or a superior direction.

* * * * *